United States Patent [19]

Sipos

[11] Patent Number: 5,352,682
[45] Date of Patent: Oct. 4, 1994

[54] COMPOSITIONS CONTAINING SALTS OF BILE ACID-AMINOSALICYLATE CONJUGATES

[75] Inventor: Tibor Sipos, Lebanon, N.J.

[73] Assignee: Digestive Care Inc., Lebanon, N.J.

[21] Appl. No.: 27,693

[22] Filed: Mar. 8, 1993

[51] Int. Cl.$^5$ .............................................. A61K 31/56
[52] U.S. Cl. ..................... 514/182; 552/553; 552/554; 424/451; 514/788.1
[58] Field of Search ............... 552/590, 591, 592, 548, 552/549, 550, 551, 553, 554; 514/182, 623, 169, 926, 927, 928, 171, 788.1; 564/188; 424/451

[56] References Cited

U.S. PATENT DOCUMENTS

| | | | |
|---|---|---|---|
| Re. 30,910 | 4/1982 | Weigand | 424/238 |
| 3,004,893 | 10/1961 | Martin | 167/73 |
| 4,079,125 | 3/1978 | Sipos | 424/32 |
| 4,280,971 | 7/1981 | Wischniewski | 264/15 |
| 4,565,810 | 6/1986 | Castagnola et al. | 514/182 |
| 4,810,422 | 3/1989 | Hatono et al. | 260/397.1 |
| 4,826,679 | 5/1989 | Roy | 424/94.21 |
| 4,828,843 | 5/1989 | Pich et al. | 424/480 |
| 4,865,765 | 9/1989 | Reiner | 552/551 |
| 4,892,868 | 1/1990 | Castagnola et al. | 514/182 |

FOREIGN PATENT DOCUMENTS

| | | | |
|---|---|---|---|
| 3184993 | 8/1991 | Japan | 552/551 |
| 1296944 | 11/1972 | United Kingdom . | |
| 1362365 | 8/1974 | United Kingdom . | |
| 2036558 | 7/1980 | United Kingdom | 514/182 |

OTHER PUBLICATIONS

Merck Index 10th Edition, 1983, p. 1413, 9695.

*Primary Examiner*—Shailendra Kumar

[57] ABSTRACT

Disclosed are compositions containing bile acid-aminosalicylate conjugates having the formula, or a pharmaceutically acceptable salt thereof

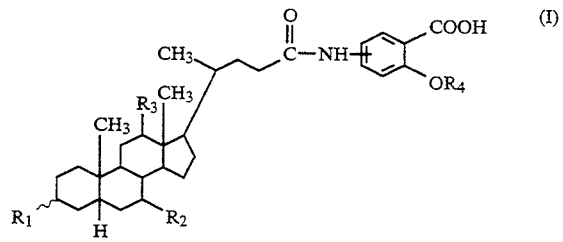

wherein
$R_1$ is OH either the $\alpha$ or the $\beta$ position;
$R_2$ is OH;
$R_3$ is H or OH; and
$R_4$ is H or acetyl, the process for their preparation and method of treating/preventing gastrointestinal disorders, impaired liver function, autoimmune diseases of the liver and biliary tract, colon cancer, inflammatory bowel diseases, Crohn's disease, cystic fibrosis, dissolving gallstones, and regulating dietary cholesterol absorption by administering said compositions to a mammal in need of such treatment.

4 Claims, No Drawings

COMPOSITIONS CONTAINING SALTS OF BILE ACID-AMINOSALICYLATE CONJUGATES

BACKGROUND OF THE INVENTION

FIELD OF THE INVENTION

This invention relates to a composition of matter consisting of salts of bile acid-aminosalicylate conjugates for ingestion by a mammal, a process for preparing said compositions, and a method for treating gastrointestinal disorders, impaired liver function, autoimmune diseases of the liver and biliary tract, prevention of colon cancer, inflammatory bowel disease, Crohn disease, ulcerative colitis, cystic fibrosis, dissolving gallstones, and regulating dietary cholesterol absorption by administering said compositions to a mammal in need of such treatment.

REPORTED DEVELOPMENTS

It is known in the prior art that ursodeoxycholic acid (hereinafter sometimes referred to as UDCA) administered to mammals can remedy various diseased conditions of the liver, gallstones, liver toxicity due to toxic metabolites, alcohol induced hang-over, drug related toxicity, colon cancer, deficiency associated with poor digestion of fats and lipids in the intestines and improvement of the nutritional state of patients having cystic fibrosis caused by hepatobiliary complications. Published examples are: "Ursodeoxycholic Acid Dissolution of Gallstones in Cystic Fibrosis", Sahl, B., Howat, J., Webb, K., *Thorax*, 43:490-1 (1988); "Effects of Ursodeoxycholic Acid Therapy for Liver Disease Associated with Cystic Fibrosis", Columbo, C., Setchell, K. D., Podda, M., Crosignani, A., Roda, A., Curcio, L., Ronchi, M. and Giunta, A., *The Journal of Pediatrics*, 117:482-489 (1990); "Effects of Ursodeoxycholic Acid Treatment on Nutrition and Liver Function in Patients with Cystic Fibrosis and Longstanding Cholestasis", Cotting, J., Lentze, M. J. and Reichen, J., *Gut* 31:918-921 (1990)).

Also, UDCA has recently gained acceptance as an effective therapeutic modality to dissolve small to medium size cholesterol gallstones in gallstone afflicted patients. Examples are found in the following references: "The Effect of High and Low Doses of Ursodeoxycholic Acid on Gallstone Dissolution in Humans", Salen, G., Colalillo, A., Verga, D., Bagan, E., Tint, G. S. and Shefer, S., *Gastro.*, 78:1412-1418 (1980); "Ursodeoxycholic Acid: A Clinical Trial of a Safe and Effective Agent for Dissolving Cholesterol Gallstones", Tint, G. S., Salen, G., Colalillo, A., Graber, D., Verga, D. Speck, J. and Shefer, S., *Annals of Internal Medicine*, 91:1007-1018 (1986); "Clinical Perspective on the Treatment of Gallstones with Ursodeoxycholic Acid", Salen, G., *J. Clin. Gastroenterology*, 10 (Suppl. 2):S12-17 (1988); "Nonsurgical Treatment of Gallstones", Salen, G. and Tint, G. S., *New England J. Med.*, 320:665-66 (1989); and "Reducing Cholesterol Levels", A. H. Weigand, U.S. Pat. No. 3,859,437).

UDCA possesses desirable biological characteristics in the upper intestine, including the following: (1) it is readily absorbed from the intestine; (2) it inhibits cholecystokinin release by the intestinal mucosa, thus ameliorating pain and producing symptomatic relief; 3) being cytoprotective it enhances the flow of bile which cleanses the liver cells from accumulated toxic metabolites and thus reduces liver toxicity and autoimmune diseases of the liver and biliary tract; 4) it prevents the binding and absorption of deoxycholic and lithocholic acids in the colon, thus effectively interfering with colon cancer development; 5) it prevents the crystallization of cholesterol into gallstones; 6) it emulsifies fats; and 7) it facilitates the hydrolysis of fat globules.

5-Aminosalicylic acid (hereinafter sometimes referred to as 5-ASA) is a well recognized anti-inflammatory agent. It interferes with prostaglandin metabolism, both through the lipoxygenase pathways, i.e. prostenoids and through the cyclooxygenase pathways, i.e., leukotrienes and hydroxyeicosatetraenoic acids, platelet-activating factor and oxygen radical production. 5-ASA diminishes inflammation by reducing the production of inflammatory mediators by the colon.

5-ASA is the active anti-inflammatory ingredient of Sulfasalazine (Sulfapyridine-5-ASA) which is being prescribed to patients afflicted with Crohn's disease, ulcerative colitis, and generalized inflammation of the gastrointestinal tract.

While the singular administration of 5-ASA can result in a minimal systemic anti-inflammatory effect throughout the body, the magnitude of the localized effect in the colon is negligible. Administration of large doses of 5-ASA, for example 10 to 15 g/day, to patients in need of therapy may result in gastrointestinal ulcerations that can further aggravate the severity of the disease. Therefore, this approach has not gained utility in the managment of ulcerative colitis and Crohn's disease.

One method to treat ulcerative colitis or Crohn's disease is to target the colon with an enteric coated 5-ASA which is released in the lower intestine and the colon. However, the required doses to achieve significant therapeutic effect is large (about 5 g/day) and some patients cannot tolerate this large dosage.

SUMMARY OF THE INVENTION

Because of the beneficial anti-inflammatory properties of 5-ASA and the known specific binding and cytoprotective effect of UDCA to intestinal receptor cells, it is highly desirous to combine these important pharmacological activities into a single entity of UDCA-5-ASA.

It has now been surprisingly discovered that by chemically linking 5-ASA through the 5-amino group by an amide linkage to the carboxyl group of UDCA, one can prepare a UDCA-5-ASA conjugate that has hitherto unexpected and potent localized anti-inflammatory and cytoprotective effects.

Therefore, one object of the present invention is to provide preparative methods for the synthesis of bile salt-5-ASA suitable for incorporation into biospheres and microtablets.

A further object of the present invention is to provide a process for the preparation of a polymer-coated bile acid-5-ASA salts in the form of microspheres, microtablets, caplets, capsugels, and other pharmaceutically acceptable dosage forms that masks the bitter taste associated with the bile salts.

Still a further object of the present invention is to provide a method for treating ulcerative colitis, Crohn's disease and bile salt deficiencies associated with biliary diseases in mammals, such as the presence of gallstones, liver toxicity due to toxic metabolites and autoimmune diseases of the liver and biliary tract, alcohol induced hang-over, drug related toxicity, deficiency associated with poor digestion of fats and lipids in the intestine and regulating dietary cholesterol absorption.

In one preferred composition of the present invention the bile acid-5-ASA salt is microencapsulated or microtableted, sealed with an intestinal juice degradable polymer to mask the bitter taste associated with bile salts, thereby increasing patient compliance in taking the medication. The microspheres uniformly disperse with food in the stomach and deliver a high level of the bile acid-5-ASA salt via the intestine to the colon. The 5-ASA and the UDCA are liberated from UDCA-5-ASA by the enzymatic action of the colonic bacteria. The liberated 5-ASA exerts its cytoprotective effect by competitively binding to bile acid receptors and preventing the reabsorption of toxic and co-carcinogenic secondary bile acids, i.e., deoxycholic acid and lithocholic acid. The liberated 5-ASA prevents production of inflammatory metabolites from arachidonic acid by the mucosal cells and reduces inflammation. Thus, the combined beneficial effects of UDCA and 5-ASA results in an unexpectedly efficacious localized cytoprotective and anti-inflammatory therapy in the lower gastrointestinal tract.

The present invention will be described with particular reference to UDCA-5-ASA and salts of UDCA-5-ASA, however, it is to be understood that other bile acid aminosalicylate conjugates, for example Ursodeoxycholic acid-4-ASA (UDCA-4-ASA), Ursodeoxycholic acid-3-ASA (UDCA-3-ASA), Chenodeoxycholic acid-5-ASA (CDCA-5-ASA), Chenodeoxycholic acid-3-ASA (CDCA-3-ASA), Cholic acid-5-ASA (CA-5-ASA), Cholic acid-4-ASA (CA-4-ASA) and Cholic acid-3-ASA (CA-3-ASA) may be used as well, which will become obvious to one skilled in the art as the description of the invention proceeds.

The compounds of the present invention have the following formula

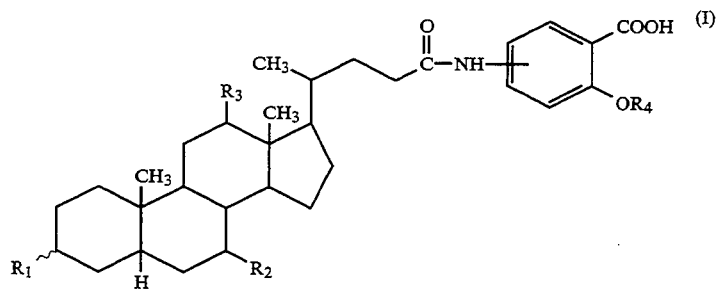

or a pharmaceutically acceptable salt thereof, wherein
$R_1$ is OH either the $\alpha$ or the $\beta$ position;
$R_2$ is OH;
$R_3$ is H or OH; and
$R_4$ is H or acetyl.

Other naturally occurring bile acids, their hydroxyl epimers and oxo-derivatives which can be hydrolyzed to a bile acid moiety by intestinal bacteria may also be utilized in the present invention.

Preferred compounds of the present invention are shown in Table I.

TABLE I

| Parent Bile Acid | $R_1$ | $R_2$ | $R_3$ | $R_4$ | Amide Derivative of | Chemical Name |
|---|---|---|---|---|---|---|
| UDCA | α-OH | β-OH | H | H | 3-ASA | Ursodeoxycholic acid-3-aminosalicylic acid amide |
| UDCA | α-OH | β-OH | H | H | 4-ASA | Ursodeoxycholic acid-4-aminosalicylic acid amide |
| UDCA | α-OH | β-OH | H | H | 5-ASA | Ursodeoxycholic acid-5-aminosalicylic acid amide |
| CDCA | α-OH | α-OH | H | H | 3-ASA | Chenodeoxycholic acid-3-aminosalicylic acid amide |
| CDCA | α-OH | α-OH | H | H | 4-ASA | Chenodeoxycholic acid-4-aminosalicylic acid amide |
| CDCA | α-OH | α-OH | H | H | 5-ASA | Chenodeoxycholic acid-5-aminosalicylic acid amide |
| CA | α-OH | α-OH | α-OH | H | 3-ASA | Cholic acid-3-aminosalicylic acid amide |
| CA | α-OH | α-OH | α-OH | H | 4-ASA | Cholic acid-4-aminosalicylic acid amide |
| CA | α-OH | α-OH | α-OH | H | 5-ASA | Cholic acid-5-aminosalicylic acid amide |
| DA | α-OH | H | OH | H or acetyl | 3-ASA | Deoxycholic acid-3-acetyl-aminosalicylic acid amide (7-DA-3-AASA) |
| DA | α-OH | H | OH | H or acetyl | 4-ASA | Deoxycholic acid-4-acetyl-aminosalicylic acid amide |
| O DA | α-OH | H | OH | H or acetyl | 5-ASA | Deoxycholic acid-5-acetyl-aminosalicylic acid amide |

The most preferred biologically active compound of the present invention is (3, 7B-dihydroxy-5B-cholan-24-oic acid-5-aminosalicylic acid), (UDCA-5-ASA).

DETAILED DESCRIPTION OF THE INVENTION

The compounds of the present invention may be prepared according the Scheme shown for UDCA-5-ASA conjugate.

Scheme

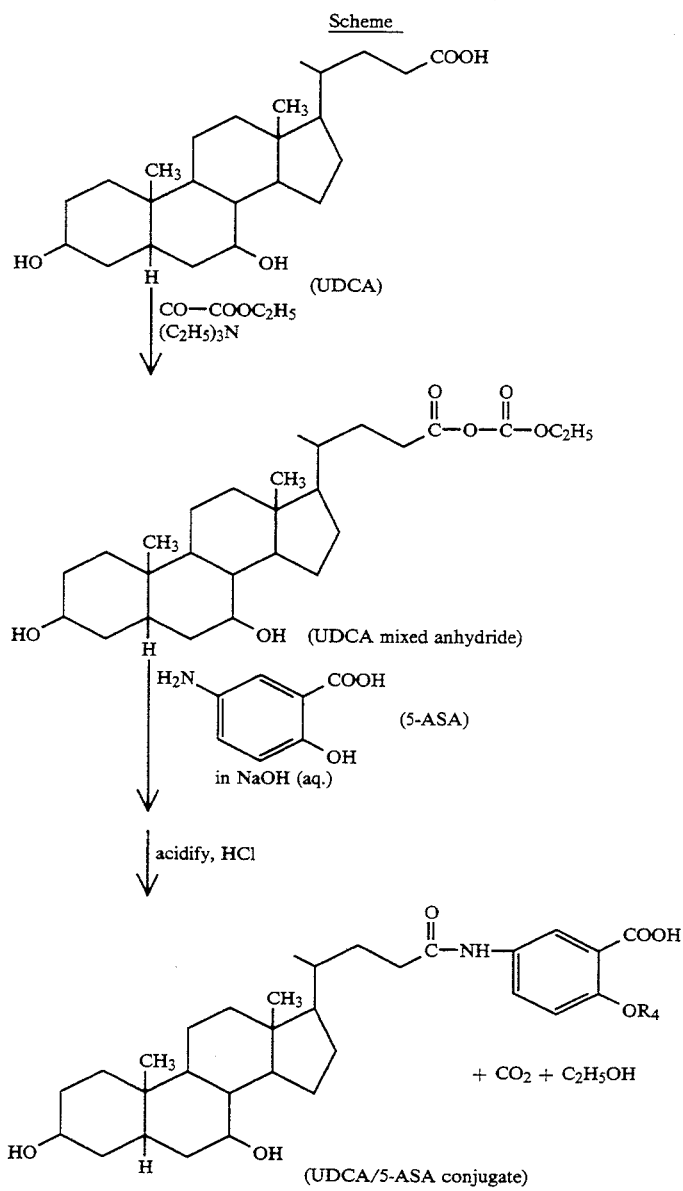

Synthesis of Active Compounds

The active compounds of the present invention are prepared by the steps of.
- dissolving a bile acid in an organic solvent and forming the bile acid anhydride by the addition of an activating agent and a catalyst;
- dissolving a salicylic acid derivative in an aqueous base;
- reacting the bile acid anhydride with the salicylic acid derivative by adding the salicylic acid derivative solution to the bile acid anhydride solution to form a reaction mixture;
- acidifying the reaction mixture to obtain a precipitate;
- filtering the precipitate to obtain a solid, redissolving the solid precipitate in a suitable solvent and let it stand overnight for obtaining pure crystals of the bile acid-ASA conjugate.

In the synthesis of the active compounds and salts of the active compounds the organic solvents which can be used include dioxane, dimethyl formamide and dimethyl sulfoxide; the activating agent may be ethyl chloroformate; the catalyst may be triethylamine; the aqueous base is aqueous NaOH or aqueous KOH; the solvent in which the precipitate is dissolved may be ethanol or methanol.

Synthesis of the Salts of Active Compounds

Salts of the bile acid-ASA conjugates are prepared by the steps of:
- dissolving the bile acid-ASA conjugate in a suitable organic solvent;
- reacting the bile acid-ASA conjugate with a methanolic solution of sodium methoxide (NaOMe) by slowly adding the NaOMe or an alkaline hydroxide to the solution containing the bile acid-ASA conjugate; and
- evaporating the organic solvent to obtain the salt of bile acid-ASA, such as the UDCA-5-ASA-Na.

The following examples will further illustrate the synthesis of the compounds and the preparation of their salts of the present invention.

EXAMPLE 1

Synthesis of 5-ASA Conjugate of Ursodeoxycholic Acid (UDCA-5-ASA)

20 gm (0.051 mole) of UDCA was dissolved in 200 ml dioxane or dimethyl formamide (DMF) containing 8 ml (0.0574 mole) triethylamine. To the solution, 4.8 ml (0.050 mole) of ethyl chlorocarbonate was added at 10° C. After stirring 15 minutes, a solution of 11.8 gm (0.077 mole) of 5-ASA in 70 ml 1.5 N sodium hydroxide was added, and the mixture was allowed to stand at room temperature for 3 hours while carbon dioxide evolved. The reaction mixture was diluted with excess cold water and acidified with 50% hydrochloric acid to pH<1. The resulting precipitate was filtered, washed thoroughly with water, and dried. Further purification of the crude product was achieved by recrystallization form a mixture of methanol/ethylacetate, or by employing silica gel column chromatography.

The crude solid (approximately 28 gm) was adsorbed over 50 gm silica gel (Merck & Co., 230–400 mesh) and chromatographed over 600 gm silica gel. Elution was carried out with ethyl acetate followed by increasing proportions of methanol. Pure compound (light brown powder) was obtained in fractions containing 5%–15% methanol in ethyl acetate (total 6 liter volume of eluant). Yield, 25 gm. Melting point, 232°–238° C. with decomposition. Infrared and NMR spectras confirmed the identity of UDCA-5-ASA.

EXAMPLE 2

Synthesis of 5-ASA Conjugate of Chenodeoxycholic Acid (CDCA-5-ASA)

The mixed anhydride was synthesized according to the method for the synthesis of ursodeoxycholic acid described in Example 1 except that chenodeoxycholic acid (20 gm) was used in place of ursodeoxycholic acid. The mixed anhydride was formed as a white precipitate. The mixed anhydride was treated with a solution of 5-ASA (10.8 gm) in 70 ml of 1N sodium hydroxide exactly as described for the synthesis of 5-ASA conjugate of ursodeoxycholic acid and was similarly purified. After crystallization, beige colored microscopic crystals of 5-ASA conjugate of chenodeoxycholic acid were obtained (total yield, 82.9%). Infrared analysis confirmed the identity of the title compound.

EXAMPLE 3

Synthesis of 5-ASA Conjugate of Cholic Acid

The mixed anhydride was synthesized according to the method for the synthesis of the mixed anhydride from ursodeoxycholic acid described in Example 1 except that cholic acid (20 gm) was used in place of ursodeoxycholic acid. The mixed anhydride was formed as a white precipitate. The mixed anhydride was treated with a solution of 5-ASA (10.6 gm) in 70 ml of 1N sodium hydroxide exactly as described for the synthesis of 5-ASA conjugate of ursodeoxycholic acid, and was similarly purified. After crystallization, beige colored microscopic crystals of 5-ASA conjugate of cholic acid were obtained (total yield, 84.9%). Infrared analysis confirmed that identity of the title compound.

EXAMPLE 4

Synthesis of 4-ASA Conjugate of Ursodeoxycholic Acid

The mixed anhydride was synthesized according to the method for the synthesis of the mixed anhydride from ursodeoxycholic acid described in Example 1. The mixed anhydride was formed as a white precipitate. The mixed anhydride was treated with a solution of 4-ASA (10.8 gm) in 70 ml of 1N sodium hydroxide exactly as described for the synthesis of 5-ASA conjugate of ursodeoxycholic acid, and was similarly purified. After crystallization, almost colorless microscopic crystals of 4-ASA conjugate of ursodeoxycholic acid were obtained (total yield, 82.7%). Infrared analysis confirmed the identity of the title compound.

EXAMPLE 5

Preparation of Salts of Ursodeoxycholic Acid-5-ASA

UDCA-5-ASA was converted to the sodium, potassium or tromethamine salts (UDCA-5-ASA-Na, UDCA-5-ASA-K or UDCA-5-ASA-tromethamine) by dissolving UDCA-5-ASA in a suitable solvent, and titrating with a water-soluble alkaline hydroxide sodium methoxide carbonate, bicarbonate or buffer solution (for example, sodium hydroxide, sodium carbonate, sodium bicarbonate, potassium hydroxide, potassium methoxide, potassium carbonate, potassium bicarbonate solutions and tromethamine (tris hydroxymethyl aminomethane) until the pH has reached 8.0–8.5. The solvent was removed by evaporation, distillation, spray drying or lyophilization, and the resultant solids were purified.

Example 6 shows the general formula for the composition of the present invention.

EXAMPLE 6

Compositions of Microsphere Forms of Bile Acid-Salicylic Acid Conjugates or a Pharmaceutically Acceptable Salt Thereof

| Ingredients | % w/w |
| --- | --- |
| Bile Acid-Aminosalicylic Acid Conjugate or a Pharmaceutically Acceptable Salt Thereof | 89.0–60.0 |
| Buffering Agent (Anhydrous) | 0.25–10.0 |
| Adhesive Polymer | 2.0–19.0 |
| Disintegrant | 1.0–8.0 |
| Gastric Acid-Resistant Polymer Coat/Talc Mixture | 8.0–16.0 |

The composition of the present invention comprises a salt of bile acid amino-salicylic acid conjugate, such as the sodium salt, a buffering agent, a suitable binder, disintegrant and a gastric acid-resistant polymer-coating that protects the composition against gastric acidity during gastric transit into the duodenum and eliminate the bitter taste associated with bile salts. Suitable salts of bile acid-aminosalicylic acid conjugates include sodium, potassium and tromethamine (trishydroxyaminomethane) salts.

Process of Making Microspheres

The process for the preparation of the microspheres comprises the steps of:
a) blending dry, powdery ingredients selected form the group consisting of (i) from about 40 to about 95% w/w bile salt-aminosalicylate conjugates; (ii) from about 0.25 to about 10% of a buffering agent selected from the group consisting of sodium carbonate (anhydrous), sodium bicarbonate (anhydrous), potassium carbonate (anhydrous), potassium bicarbonate (anhydrous) and tromethamine or a mixture thereof; and (iii) from about 1.0 to about 8% w/w of a disintegrant selected from the group consisting of starch and modified starches, microcrystalline cellulose and propylene glycol alginate; and from about 2.0 to about 19% w/w of a liquid adhesive polymer selected from the group consisting of polyvinylpyrrolidone, hydroxypropyl cellulose, cellulose acetate phthalate, and methyl cellulose;

b) wetting said blended ingredients with a liquid to cause the blend to stick together, wherein said liquid is selected from the group consisting of: methanol, ethanol, 2-propanol, acetone, ethylacetate and mixtures of: methanol/2-propanol/water (1%–25%: 75%–99%: 0.05%–1.5%); ethanol/2-propanol/water (1%–25%: 75%–99%: 0.05%–1.5%); 2-propanol/water (98%–99.9%: 0.05%–1.5%); methanol/water/2-propanol/ethyl acetate (1%–25%: 0.05%–1.5%: 75%–98%: 1%–5%).

c) granulating or extruding the liquid-wetted blend through a 10 or 18 mesh S/S screen to sieve granules using an oscillating/reciprocating granulator or a twin-screw extruder at a medium-to-high speed;

d) converting the granules to a uniform diameter particle size in a "unisizer vessel" that rotates at 15 to 45 rpm for about 5 to 10 minutes;

e) compacting the uniform particles to spherical particles in a marumerizer, which is essentially a cylindrical vessel with a rotating disk at the bottom for a period of 15 to 90 seconds. An alternate method of compacting the microspheres can also be achieved in a rotating conventional coating pan. In this case, the particles are tumbled in the pan for 15–30 minutes, occasionally wetting the particles with a fine mist of the liquid adhesive polymer composition, followed by slowly dusting the bile acid-ASA/buffer/disintegrant composition onto the tumbling and flowing microspheres to prevent aggregation and formation of duplets;

f) drying the spherical particles in an oven overnight under a stream of dry air not exceeding 75° C. and about 40% relative humidity;

g) separating the spherical particles if not of uniform size according to desired sizes using U.S. Standard sieve screens;

h) coating the particles first with an intestinal juice degradable polymer coating, which is comprised of from about 1.5% to about 20% of methyl cellulose and from about 0.5% to about 15% of poly(hydroxyethyl methacrylate) and from about 0.2 to about 2% of a suitable plasticizer;

i) drying the polymer-coated spherical particles in an oven overnight under a stream of dry air, not exceeding 75° C. and 40% relative humidity, to remove all the volatile substances (moisture and solvents).

The following formulation examples will further serve to illustrate the compositions of the present invention, wherein the compositions and process of preparing them will be described with specific reference to microsphere form. However, it is to be noted that microtablet and caplet forms of the composition and the process of making them is also intended to be covered by the present invention. The process of making the microtablet and caplet forms of the composition is analogous to that of making the microspheres with the exception that the 20 to 80 mesh particles are compressed together into microtablets of 0.5 mm to 2.5 mm diameters, and 4 mm to 8 mm in the case of caplets, with a suitable tablet press and them polymer-coated as described above in Steps h through i)

EXAMPLE 7

Formula Composition (Microspheres)

| Ingredients | A (uncoated) % w/w | B (coated) % w/w |
| --- | --- | --- |
| Disintegrant | 6.0 | 5.2 |
| UDCA-5-ASA (Na, K, tromethamine) | 89.0 | 76.7 |
| Adhesive Polymer | 5.0 | 4.3 |
| Gastric Acid-Resistant Polymer coat/talc mixture | | 13.8 |

The microspheres of this Example were prepared by employing a conventional coating pan. The microspheres were built up to larger particle sizes by placing the bile salt-5-ASA-containing 30 to 40 mesh starting seeds in the rotating coating pan, wetting the microspheres with the liquid/adhesive polymer-containing mixture, followed by slowly dusting the UDCA-5-ASA/buffer/disintegrant composition over the tumbling and flowing bile salt-5-ASA-containing seeds. The sequence of these steps is repeated until the seeds are built up into microspheres having diameters in the range of 10 to 20 mesh, preferably 14 to 16 mesh.

EXAMPLE 8

Formula Composition (Microtablets and Caplets)

| Ingredients | A (uncoated) % w/w | B (coated) % w/w |
| --- | --- | --- |
| Disintegrant | 3.0 | 2.7 |
| UDCA-5-ASA | 87.0 | 77.1 |
| Buffering Agent (Anhydrous) | 6.0 | 5.9 |
| Adhesive Polymer | 3.0 | 2.7 |
| Lubricant (Stearic Acid) | 1.0 | 0.9 |
| Gastric Acid-Resistant Polymer coat/talc mixture | | 10.7 |

The microtablets of this Example were prepared by the following procedure: 1) the dry blend of bile acid-aminosalicylic acid conjugate/buffer/disintegrant was ground in a centrifugal mill or impact pulverizer to a uniform particle size; 2) the powdery mix is sprayed with a fine mist of the adhesive polymer/liquid mixture; 3) the composition is dried, followed by blending the dried composition with a lubricant and compressing the free flowing powder into microtablets of 1.5 mm x 2.0 mm diameters with appropriate punches and dies and with a suitable tableting press as described in U.S. Pat. No. 4,828,843 (Pich et al) which is hereby incorporated by reference. The microtablets are polymer coated as described previously in Example 6.

Reference is now made to the specific ingredients used in the above Examples 6 through 8.

Disintegrants:

Explotab (Mendell, Inc.) and microcrystalline cellulose.

Buffering Agents:

Sodium carbonate (anhydrous), sodium bicarbonate (anhydrous), potassium carbonate (anhydrous), potassium bicarbonate(anhydrous) and tromethamine (USP).

Adhesive Polymeric Agents:

Hydroxypropyl cellulose (Klucel HF, Hercules Co.), polyvinylpyrrolidone (Plasdone, GAF Co.), a 60:40 blend of methyl cellulose and ethyl cellulose (Dow Chem. Co.), hydroxypropyl methyl cellulose (Grades 50 and 55, Eastman Kodak Co.), cellulose acetate phthalate (Eastman Kodak Co.).

Acid-Resistant Polymers:

To coat the biospheres: hydroxypropyl methyl cellulose phthalate, Grades 50 and 55 (Eastman Kodak Co., or Shin-Etsu Chemical Co., Ltd.), cellulose acetate phthalate (Eastman Kodak Co.), Eudragit® (Rohm Pharma GMBH) and Aquacoat® (FMC Corp.). Example 9 will further illustrate a typical composition of the acid-resistant polymer coating.

Plasticizers for Polymer Coating:

Diethyl phthalate, glycerol triacetate and acetylated triglycerides, both unsaturated and saturated.

EXAMPLE 9

Compositions of Gastric Acid-Resistant Polymeric Coating Solution

| Ingredients | % w/w |
| --- | --- |
| Cellulose Acetate Phthalate (CAP) | 7.5 |
| Diethyl Phthalate (DEP) | 2.0 |
| Isopropyl Alcohol (IPA) | 45.0 |
| Ethyl Acetate (EtOAc) | 45.0 |
| Talc, USP | 0.5 |

The gastric acid-resistant polymer solution was prepared by dissolving the cellulose acetate phthalate in a solvent mixture of isopropyl alcohol and ethyl acetate, followed by the addition of diethyl phthalate and talc.

When the cellulose acetate phthalate was replaced with hydroxypropyl methyl cellulose phthalate, an equally suitable acid-resistant polymer-coating was obtained. The presence of talc in the film-forming polymer coating solution helps to prevent the aggregation of the microspheres.

In one modification of the coating procedure, the UDCA-5-ASA microspheres were first sealed with an initial coat of cellulose acetate phthalate/diethyl phthalate/talc/solvent mix to protect the composition from moisture, followed by a secondary coating with an aqueous polymeric latex dispersion (Aquecoat® or Eudragit®). The employment of the aqueous coating composition, as a secondary coating in place of the solvent based coating, is more cost effective and reduces environmental pollution by the evaporated solvents.

EXAMPLE 10

Compositions of the Intestinal Juice Degradable Polymeric Coating Solution

| Ingredients | % w/w |
| --- | --- |
| Methyl Cellulose | 1.5–20 |
| Poly(Hydroxyethyl Methacrylate), poly(HEMA) | 0.5–15 |
| Plasticizer | 0.2–2 |
| Solvent Mixture of Example 9, q.s. to 100 g | |

EXAMPLE 11

When the methyl cellulose was replaced with a 1:1 blend of an aqueous methyl cellulose/ethyl cellulose latex microemulsion an equally suitable intestinal juice degradable polymeric film was obtained.

Biological experiments were conducted in order to ascertain physiological activity of the compounds and compositions of the present invention.

EXAMPLE 12

Hydrolysis of 5-ASA Conjugate of Ursodeoxycholic Acid with Bacterial Enzyme Cholylglycine Hydrolase 1 mg of 5-ASA conjugate of ursodeoxycholic acid (UDCA-5-ASA) was incubated with 2 ml acetate buffer, pH 5.6, and 1 ml each of a 1.85% solution of EDTA and 0.87% mercaptoethanol for 10 min at 37° C. Five units of cholylglycine hydrolase enzyme (from Clostridium perfringens) was added, and the mixture incubated at 37° C. for 18 hours. The reaction mixture was analyzed for hydrolysis products by thin layer chromatography. The results showed that the UDCA-5-ASA compound was completely deconjugated into its components, thereby showing that the intestinal bacterial enzymes hydrolyzed the 5-ASA conjugate of ursodeoxycholic acid to free 5-ASA and UDCA.

EXAMPLE 13

Intestinal Absorption of Salts of 5-ASA Conjugate of Ursodeoxycholic Acid (UDCA-5-ASA-Na)

Three hours after creation of bile fistula in 2 rats, a bolus of 40 mg of sodium salt of 5-ASA conjugate of ursodeoxycholic acid was infused in 1 ml saline solution. Bile was collected hourly for 2 hours before, and 3 hours after infusion of the compound, and analyzed for free 5-ASA and free ursodeoxycholic acid, and its 5-ASA conjugate (UDCA-5-ASA) by HPLC and GLC (as methyl estertrimethylsilyl ether derivatives). Less than 2% of the infused dose of the UDCA-5-ASA conjugate was recovered in the bile in the 3 hours after infusion, and no free ursodeoxycholic acid was found in the bile. This showed that 5-ASA conjugate of ursodeoxycholic acid (UDCA-5-ASA) is poorly absorbed from the intestine into the bile tract.

EXAMPLE 14

Protocol for Feeding Sodium Salt of the 5-ASA Conjugate of Ursodeoxycholic Acid (UDCA-5-ASA-Na) to Rats The sodium salt of 5-ASA conjugate of ursodeoxycholic acid was mixed in rat chow at a 1% concentration, and fed to 2 rats for a period of 4 days. Rats consumed an average of 28 gm of food (equivalent to 280 mg of the compound per day). Feces were collected daily for fecal bile acid determination (14A). At the end of 4 days, bile fistula was constructed, and bile was collected for a period of 1 hour after which the rats were sanguinated. Daily, feces were freeze-dried and weighed (daily fecal weight, 7± gm). Two control rats were given rat chow without added bile acid and identical experiments were performed. Each dried fecal sample (from the control and bile acid fed animals) was thoroughly ground, and 500 mg of each specimen was thoroughly extracted overnight with 1% ammoniacal ethyl alcohol. After removal of solvent, the residue was taken up in methanol and divided into 2 equal aliquots: each aliquot was analyzed for free and conjugated ursodeoxycholic acid by a combination of HPLC and GLC (as methyl ester-trimethylsilyl ether derivatives). The first aliquot was analyzed without further treatment to find the proportions of free as well as conjugated (with glycine, taurine or 5-ASA) ursodeoxycholic acid. The second aliquot was first subjected to rigorous alkaline hydrolysis (3 N sodium hydroxide for 4 hours at 120° C.), and the total amount of liberated free ursodeoxycholic acid was determined. Bile samples (14B) from experimental rats, as well as control rats, were similarly analyzed for free and conjugated ursodeoxycholic acid by HPLC and GLC (as methyl ester-trimethylsilyl ether derivatives) both before and after rigorous alkaline hydrolysis.

The following results were obtained when the fecal samples were analyzed for bile acids:

EXAMPLE 14 A

| Ingredients | % w/w |
| --- | --- |
| Ursodeoxycholic Acid | 35 |
| UDCA-5-ASA | 60 |
| Deoxycholic, Lithocholic and Muricholic Acids | 5 |

The following results were obtained when the bile samples were analyzed for bile acids:

EXAMPLE 14

| Ingredients | % w/w |
| --- | --- |
| UDCA-5-ASA | 5 |
| UDCA-Taurine | 35 |

There was an increase of 4% in the amount of $\beta$-muricholic acid as compared to control rats, and a 1.5% increase in the proportion of $\omega$-muricholic acid, while deoxycholic acid, cholic acid and 1-muricholic acid were all reduced by 4%, 12% and 5% respectively from control rats. The proportions of lithocholic in the UCDA-5-ASA fed animals, as well as in the control rats, were the same. In control rats, no 5-ASA conjugate of ursodeoxycholic acid was detected; and its taurine conjugate (UDCA-5-Taurine) was found to be present in only 2.5%.

The results of the feeding study and the bile fistula infusion experiment showed that (a) 5-ASA conjugate of ursodeoxycholic acid is poorly absorbed form the intestine and is targeted to the colon, where it is partially deconjugated; (b) part of the liberated ursodeoxycholic acid is absorbed from the colon into the enterohepatic circulation, where it is conjugated with taurine by hepatic enzymes, and secreted into the bile: (c) the 5-ASA is released to protect the intestinal mucosa from insult by inflammatory substances produced by prostaglandin metabolism.

Based on these results, it is concluded that conjugation of ursodeoxycholic acid with 5-ASA is an effective way to target both ursodeoxycholic acid and 5-ASA to the enterohepatic circulation and to the colon, respectively. This, both 5-ASA and ursodeoxycholic acid will exhibit their anti-inflammatory and cytoprotective effects in the colon, as well as the liver.

Method of Treating Bile Acid Deficiency and Inflammatory Diseases of the Colon The composition of the present invention (Examples, 6, 7 and 8) are orally administrable in an effective amount to patients in needs of localized anti-inflammatory therapy for gastrointestinal diseases. UDCA-5-ASA can be administered in a suitable pharmaceutically acceptable vehicle that delivers UDCA-5-ASA to the lower intestine and the colon. Once in the lower intestine, the protective coating dissolves and the UDCA-5-ASA is released to the target site of action. 5-ASA and UDCA are liberated from UDCA-5-ASA by the enzymatic action of the colonic bacteria.

Bile acid deficiency conditions and toxic bile acid syndromes include digestive disorders, impaired liver function, autoimmune diseases of the liver and biliary tract, colon cancer, alcohol induced hang-over, drug related toxicity, deficiency associated with poor digestion of fats and lipids, cystic fibrosis, gallstones, and abnormal dietary cholesterol absorption. Inflammatory diseases include Crohn's disease, ulcerative colitis, and general inflammation of the gastrointestinal tract.

The total amount of the compositions required to be administered to a bile acid deficient patient and/or a patient having gastrointestinal inflammation will vary with the severity of the condition, age, and other physical characteristics of the patient. Physicians will prescribe the total amount, the dosage, and the frequency of administration on a patient by patient basis. Generally, for bile acid deficient patients and/or patients with inflammatory condition of the gastrointestinal tract form about 0.15 to about 2.4 gms of the composition are administered in divided doses once or twice a day.

For ease of administration of the compositions it is preferred to use gelatin capsules containing about 0.25 to 0.8 grams of microspheres. Gelatin capsules which disintegrate in the acidic environment of the stomach are well-known and utilized in the prior art. One or two capsules of the composition are swallowed and washed down with a glass of water once or twice daily, or as directed by a trained medical professional.

Young children, handicapped individuals and elderly patients are sometimes unable to swallow big gelatin capsules. Microspheres of very small sizes of the present invention could then be administered to these patients with liquid food, such as milk, apple sauce and semi-solid foods. One preferred way of administering the microspheres to small children or handicapped individuals is to empty the content of one of more gelatin capsules onto a spoon and mixing the microspheres with apple sauce then introducing into the mouth of the patient.

The compositions are tasteless, unlike the insoluble acidic form of bile acids which are associated with an offensive bitter taste. This advantage increases patient compliance in taking the medication.

Having fully described my invention, it will be apparent to one skilled in the art wherein changes and modifications can be made thereto without departing from the spirit and scope thereof.

What is claimed is:

1. A method of treating/preventing bile acid deficiency condition and inflammatory disease in a patient comprising the administration to said patient in need of such treatment/prevention an effective amount of a pharmaceutically acceptable bile acid-aminosalicylic acid conjugate of the formula (I) or a pharmaceutically acceptable salt thereof

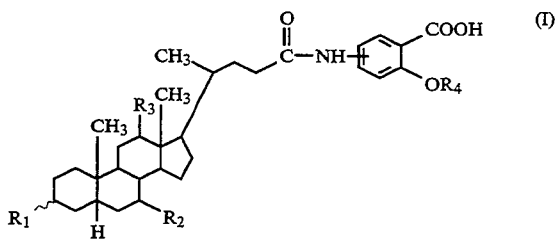

wherein $R_1$ is OH either in the $\alpha$ or in the $\beta$ position;

$R_2$ is OH;

$R_3$ is H or OH; and $R_4$ is H or acetyl.

2. A method of treating/preventing bile acid deficiency condition and inflammatory disease in a patient comprising the administration to said patient in need of such treatment/prevention an effective amount of a salt according to claim 1 wherein said pharmaceutically acceptable salt is selected from the group consisting of sodiums potassium and tromethamine.

3. A method of treating/preventing bile acid deficiency condition and inflammatory disease in a patient comprising the administration to said patient in need of such treatment/prevention an effective amount of a conjugate according to claim 1 wherein said bile acid-aminosalicylic acid conjugate is selected from the group consisting of ursodeoxycholic acid-3-aminosalicylic acid amide, ursodeoxycholic acid-4-aminosalicylic acid amide, ursodeoxycholic acid-5-aminosalicylic acid amide, chenodeoxycholic acid-3-aminosalicylic acid amide, chenodeoxycholic acid-4-aminosalicylic acid amide and chenodeoxycholic acid-5-aminosalicylic acid amide.

4. A method of treating/preventing bile acid deficiency condition and inflammatory disease in a patient comprising the administration to said patient in need of such treatment/prevention an effective amount of a conjugate according to claim 1 wherein said bile acid-aminosalicylic acid conjugate is selected from the group consisting of cholic acid-3-aminosalicylic acid amide, cholic acid-4-aminosalicylic acid amide, cholic acid-5-aminosalicylic acid amide, deoxycholic acid-3-acetylaminosalicylic acid amide, deoxycholic acid-4-acetylaminosalicylic acid amide and deoxycholic acid-5-acetylaminosalicylic acid amide.

* * * * *